United States Patent [19]

Heyman et al.

[11] Patent Number: 4,513,750

[45] Date of Patent: Apr. 30, 1985

[54] METHOD FOR THERMAL MONITORING SUBCUTANEOUS TISSUE

[75] Inventors: Joseph S. Heyman, Williamsburg, Va.; Gary H. Brandenburger, Bellevue, Wash.

[73] Assignee: The United States of America as represented by the Administrator of the National Aeronautics and Space Administration, Washington, D.C.

[21] Appl. No.: 582,492

[22] Filed: Feb. 22, 1984

[51] Int. Cl.³ .............................................. A61B 10/00
[52] U.S. Cl. ................................... 128/660; 128/736; 374/117; 374/160
[58] Field of Search ............. 128/660, 661, 804, 24 A, 128/736; 374/117, 160

[56] References Cited

U.S. PATENT DOCUMENTS

| | | | |
|---|---|---|---|
| 3,577,981 | 5/1971 | Kuris | 128/663 |
| 3,609,731 | 9/1971 | Evans | 374/117 X |
| 3,893,111 | 7/1975 | Cotter | 128/736 X |
| 4,105,018 | 8/1978 | Greenleaf et al. | 128/660 |
| 4,138,998 | 2/1979 | Nowogrodzki | 128/736 X |
| 4,246,784 | 1/1981 | Bowen | 128/736 |
| 4,315,514 | 2/1982 | Drewes et al. | 128/660 X |
| 4,323,077 | 4/1982 | Smith | 128/660 |
| 4,340,796 | 7/1982 | Yamaguchi et al. | 374/117 X |
| 4,373,532 | 2/1983 | Hill et al. | 128/660 |
| 4,390,026 | 6/1983 | Christman | 128/660 |
| 4,452,081 | 6/1984 | Seppi | 128/660 X |

*Primary Examiner*—Kyle L. Howell
*Assistant Examiner*—Francis J. Jaworski
*Attorney, Agent, or Firm*—William H. King; John R. Manning; Howard J. Osborn

[57] ABSTRACT

A noninvasive accurate method for measuring the temperature of tissue beneath the surface of a living body 11. Ultrasonic signals (14) are directed into beads 13 of a material that are inserted into the tissue with a syringe. The reflected signals (15) indicate the acoustic impedance or resonance frequency of the beads 13 which in turn indicates the temperature of the tissue. A range of temperatures around the melting temperature of the material can be measured by this method.

8 Claims, 4 Drawing Figures

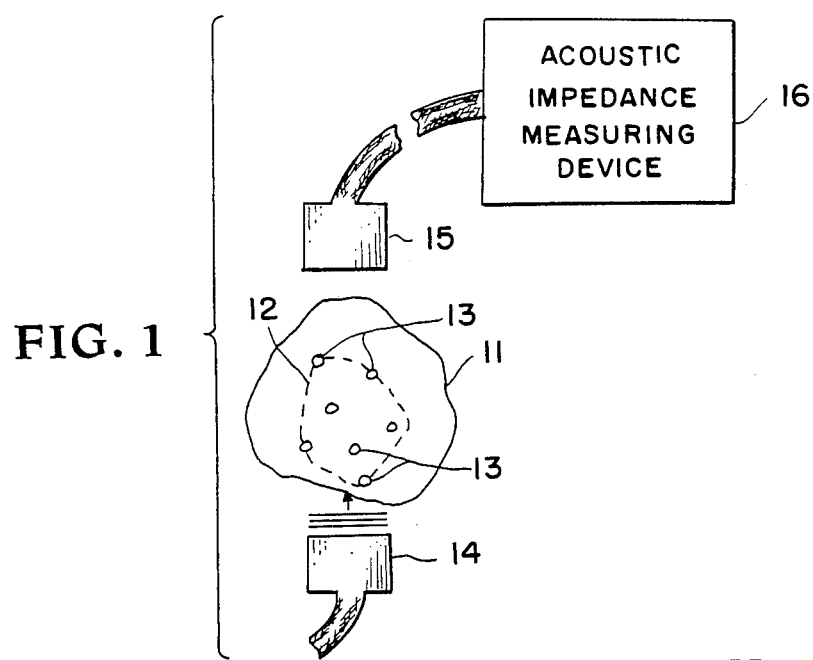
FIG. 1
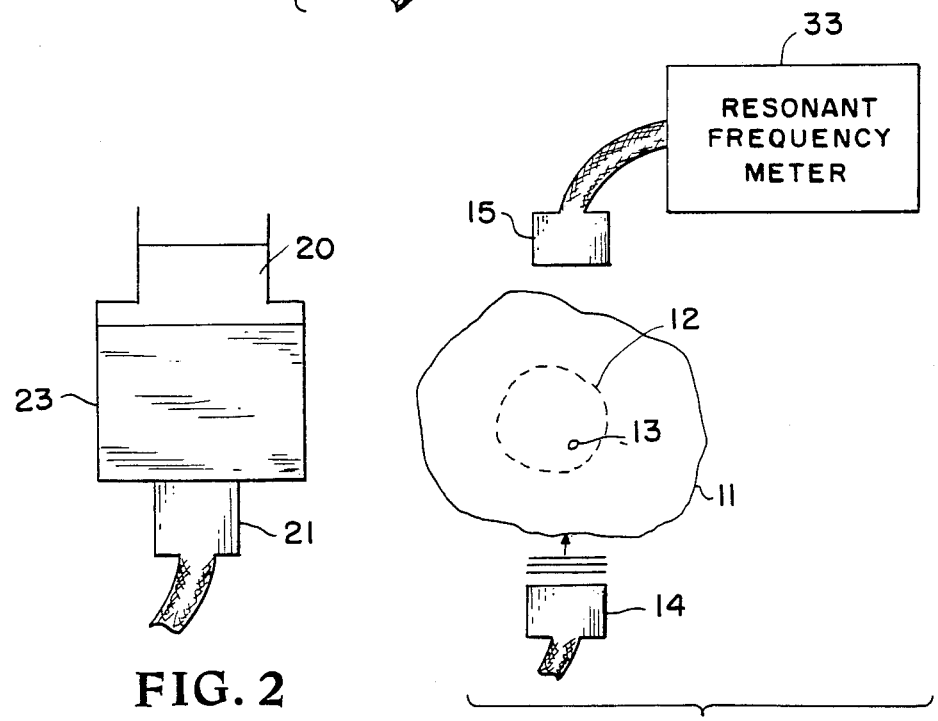
FIG. 2
FIG. 4

METHOD FOR THERMAL MONITORING SUBCUTANEOUS TISSUE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

The invention relates generally to the treatment of cancer by localized heating of the tumor cells using microwave radiation or other heating means and more specifically concerns accurately monitoring the temperature of subcutaneous tissue in the region of the tumor.

Nonsurgical elimination of malignant tumors has been approached using various techniques. Only limited success has been realized using chemotherapy and/or x-ray irradiation, and both techniques frequently elicit distressing side effects. In contrast, nonionizing microwave or ultrasonic energy are potential alternatives whose side effects may be less severe than those of ionizing radiation such as x-ray. Unlike chemotherapy which acts systematically, the side effects of microwave and ultrasound, if any, are localized. Microwave (1–10 GHz electromagnetic energy) and ultrasound waves (generally of Megahertz frequency) can be generated inexpensively without the cost, bulk, or hazards of the radiation and high voltage supplies required for x-ray.

Unlike x-ray irradiation, microwave and ultrasound destroy malignant cells strictly by localized heating of the affected region. Advantage is taken on the malignant cell's higher sensitivity to temperature relative to that of normal tissue. In addition, reduced destruction of healthy tissue is achieved by concentrating several different energy sources on the tumor region, as is done with x-ray. Significant malignant cell destruction occurs for temperatures above a threshold of 43° C. Below this threshold, however, malignant cell growth may be accelerated. Thus, careful control of temperature must be maintained in the vicinity of the tumor: Too much energy may destroy surrounding healthy tissue; too little might aggravate tumor enlargement.

Noninvasive localized temperature sensing methods such as infrared detection of skin surface temperature and microwave thermometry have proved to be unreliable indicators of the temperature in underlying tissue such as the breast. Surgically implanted, invasive temperature probes are at risk of causing tumor metastasis; this constitutes a significant hazard, particularly for breast tumors which frequently are the site of the primary malignancy. Furthermore, such probes are an infection risk and cannot be used during irradiation without resulting in localized heating. Thus, a noninvasive but accurate method for measuring the temperature of underlying tissue is required if microwave or ultrasonic irradiation is to become a viable form of cancer treatment.

It is therefore an object of this invention to provide a noninvasive but accurate technique for measuring the temperature of underlying tissue.

Another object of this invention is to provide a technique based on ultrasound for measuring tissue temperature.

A further object of this invention is to provide a technique for measuring tissue temperature suitable for use with microwave or ultrasound treatment of cancer.

Still another object of the invention is to provide a technique for measuring tissue temperature which is safe enough to permit frequent, repeated measurements without accumulated exposure hazard to either the patient or the medical staff.

A still further object of the invention is to provide a noninvasive technique for measuring tissue temperature which is accurate to within 0.5° C. over the range of 35° C. to 45° C.

Yet another object of this invention is to provide a noninvasive technique for measuring tissue temperature which is accurate over a wide range of temperatures.

Other objects and advantages of this invention will become apparent hereinafter in the specification and drawings.

SUMMARY OF THE INVENTION

The invention is a noninvasive accurate method for measuring the temperature of tissue beneath the surface of a medium such as in a living body. Beads of a material having a predetermined melting temperature are inserted into the tissue by means of a syringe. Then ultrasonic signals are focused on the beads and the acoustic impedance of the beads is determined from the reflected signals. The acoustic impedance of the beads is indicative of the state (solid, liquid ) of the beads which is indicative of the temperature of the tissue. Consequently, this invention can be used to measure a small range of temperatures around the melting temperature of the bead material.

BRIEF DESCRIPTION OF THE DRAWINGS

FIG. 1 is a schematic drawing for describing the method of this invention;

FIG. 2 is a schematic drawing for describing how the material used as the beads in FIG. 1 is calibrated;

FIG. 3 is a schematic drawing for describing a variation of and

FIG. 4 is a schematic drawing for describing a second variation of the invention.

DETAILED DESCRIPTION OF THE INVENTION

Figure 3:
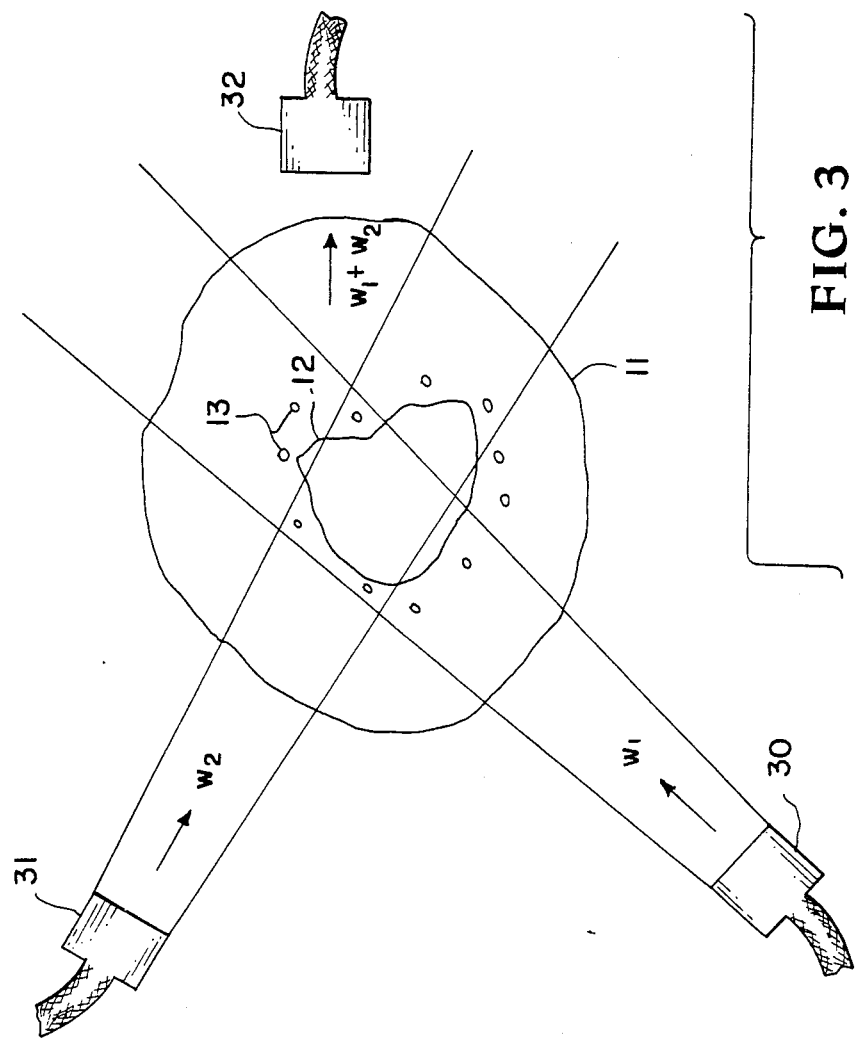

The method of ultrasonic temperature measurement utilized by this invention is demonstrated in FIG. 1. A section 11 of a human body has a tumor 12 beneath the surface. In the treatment of the tumor with microwave or other radiation, the radiation is directed into the body by equipment (not shown) to heat the tumor 12. The tumor must be heated above 43° C. to have significant malignant cell destruction. As the radiation is directed into the tumor to heat the tumor, the temperature of the tissue in the region surrounding the tumor will rise. It is necessary that the temperature in the region surrounding the tumor not substantially exceed 43° C.: healthy tissue will be destroyed if the temperature rise is too high. Consequently, the temperature surrounding the tumor must be monitored during the heating of the tumor to protect the healthy tissue. Also, the temperature surrounding the tumor will be indicative of the temperature in the tumor.

To monitor the temperature in the healthy tissue surrounding the tumor, several beads 13 of a material are inserted into the healthy tissue surrounding the tumor by means of a syringe. The material in beads 13 can be a wax or fat that has a melting temperature approximately equal to the desired maximum temperature of the healthy tissue. A high frequency transducer 14 ($\approx 2 \times 10^6$ Hz) launches bursts of sound into the body that are focused on a plane containing beads 13. The reflected sound is received by a transducer 15 and the acoustic impedance of beads 13 contained in the reflected signals is measured by a suitable acoustic impedance measuring device 16. The measured acoustic impedance of beads 13 is indicative of the temperature of the healthy tissue. That is, as beads 13 are heated the state of beads 13 will change from a solid to liquid and the acoustic impedance of beads will change. Hence, the measure of changes in acoustic impedance of beads 13 is a measure of a short range of temperatures.

Among the materials investigated for use as beads 13, phenyl solicylate has been found to have good phase transformation characteristics and its state change over the temperature gradient from 43° C. to 44° C. can be detected ultrasonically by the change in acoustic impedance.

To calibrate the change in acoustic impedance with change in temperature of beads 13, a sample 20 of the material used in beads 13 is heated by means not shown. As the material is heated, a piezoelectric ultrasonic transducer 21, coupled to the sample 20 through a glass column 23, is used in reflection to measure the acoustic impedance as a function of temperature throughout the entire solid-liquid-solid cycle of the sample 20.

To further calibrate the change in acoustic impedance with change in temperature small beads of the bead 13 material are suspended in a tissue-simulating medium and measurements are made as in FIG. 1. The acoustic impedance of the material is measured over the entire solid-liquid-solid temperature cycle.

In a variation of the method of this invention as shown in FIG. 3, a first transducer 30 directs a first frequency $W_1$ and a second transducer 31 directs a second frequency $W_2$ into beads 13 of tumor tissue. A receiver 32, including a filter for passing only the $W_1 + W_2$ or $W_1 - W_2$, receives the reflected sound. From this received signal the temperatures of beads can be determined from the nonlinear interaction of the mixed beams at their intersection site.

In a second variation of the invention as shown in FIG. 5, transistor 14 launches an ultrasonic wave to a bead 13 which has been inserted in the monitoring zone. Only one bead 13 is needed, however, several beads 13 can be used. The resonant frequency of the bead 13 depends on its temperature and its environment. The change in the resonant frequency of the bead will depend primarily on its temperature. The reflected signal is received by transistor 15 and the resonant frequency is measured by a resonant frequency meter 33. Meter 33 can be a gated swept wave in conjunction with a tracking spectrum analyzer as disclosed in U.S. Pat. No. 4,391,142. This variation of the invention can therefore measure any temperature rather than a small range around a discrete phase transition temperature.

The advantage of this invention is that it provides a noninvasive accurate method for measuring the temperature of tissue beneath the surface of a living body.

It is to be understood that the form of the invention herewith shown and described is to be taken as a preferred embodiment. Changes may be made without departing from the invention. For example, even though the reflection mode is preferred, the ultrasonic apparatus could operate in the transmission mode instead of the reflection mode as disclosed.

What is claimed is:

1. A method for monitoring temperatures about a selected temperature in any medium especially in subcutaneous tissue in a living body comprising the steps of:
   inserting beads of a material having a melting point approximately equal to said selected temperature, into said medium;
   directing ultrasonic signals at said beads; and
   receiving the ultrasonic signals reflected by said beads whereby the received signals contain information representative of the acoustic impedance of said beads which is indicative of the temperature in said medium.

2. A method for monitoring temperatures according to claim 1 including the step of measuring the acoustic impedance of said beads from said received signals.

3. A method for monitoring temperatures according to claim 1 wherein said beads are inserted into subcutaneous healthy tissue in the vicinity of a tumor whereby the temperature of the tumor can be monitored.

4. A method for monitoring temperatures according to claim 1 including the step of calibrating the change in acoustic impedance with temperature of said material.

5. A method for monitoring temperatures according to claim 1 wherein said step of directing ultrasonic signals at said beads comprises directing ultrasonic signals at said beads in only one direction.

6. A method for monitoring temperatures according to claim 1 wherein said step of directing ultrasonic signals at said beads comprises directing ultrasonic signals at a first frequency at said beads in a first direction and directing ultrasonic signals at a second frequency at said beads in a second direction and receiving the mixed scattered signal at the sum and/or difference frequency to measure the temperature at the mixing volume.

7. A method for monitoring temperatures in subcutaneous tissue comprising the steps of:
   inserting a bead of material, that changes resonant frequency with temperature, into said subcutaneous tissue;
   directing ultrasonic signals at said bead of material; and
   receiving the ultrasonic signals reflected by said bead whereby the received signal contains information representative of the resonant frequency of said bead of material which is indicative of the temperature in said subcutaneous tissue.

8. A method for monitoring temperatures according to claim 7 including the step of measuring the resonant frequency of said bead from said received signal.

* * * * *